United States Patent
Montfort et al.

(10) Patent No.: US 10,054,541 B1
(45) Date of Patent: Aug. 21, 2018

(54) FUSER RESERVOIR SENSOR TO TEST THE TURBIDITY OF THE FUSER OIL

(71) Applicant: Xerox Corporation, Norwalk, CT (US)

(72) Inventors: David Bradley Montfort, Webster, NY (US); Jason Slack, Rochester, NY (US); Barry Ayash, Webster, NY (US); Mark Allen Rule, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 15/646,766

(22) Filed: Jul. 11, 2017

(51) Int. Cl.
*G03G 15/20* (2006.01)
*G01N 21/49* (2006.01)

(52) U.S. Cl.
CPC ......... *G01N 21/49* (2013.01); *G03G 15/2025* (2013.01)

(58) Field of Classification Search
CPC ........... G03G 15/2039; G03G 15/2053; G03G 15/205; G03G 2215/2035; G03G 15/55
USPC .......................................................... 399/33
See application file for complete search history.

(56) References Cited

U.S. PATENT DOCUMENTS

| | | | |
|---|---|---|---|
| 5,864,740 A | 1/1999 | Heeks et al. | |
| 6,058,279 A | 5/2000 | Folkins | |
| 6,176,575 B1* | 1/2001 | Crawford | B41J 2/0057 347/103 |
| 2006/0060512 A1* | 3/2006 | Astle | B01D 27/101 210/85 |
| 2006/0103842 A1* | 5/2006 | Tokhtuev | G01N 21/53 356/338 |
| 2014/0131259 A1* | 5/2014 | Goldblatt | G01N 15/06 210/96.1 |
| 2015/0022570 A1* | 1/2015 | Chappell | B41J 2/125 347/6 |

* cited by examiner

*Primary Examiner* — Walter L Lindsay, Jr.
*Assistant Examiner* — Frederick Wenderoth
(74) *Attorney, Agent, or Firm* — Caesar Rivise, PC

(57) ABSTRACT

Accordingly, an improved system and method is provided with which an automatic analysis of the fuser oil is performed to prevent accidental oil and toner mismatches by the insertion of a photovoltaic sensor and associated logic inline along the tube that delivers the fuser oil to the fuser.

13 Claims, 5 Drawing Sheets

FUSER RESERVOIR SENSOR TO TEST THE TURBIDITY OF THE FUSER OIL

BACKGROUND OF THE INVENTION

The presently disclosed embodiments relate to applying release agents to fusers to facilitate heat and pressure fixing of marking particles in imaging devices such as, for example, xerographic printing devices; and, more particularly, to turbidity sensors that can be used to monitor the release agent.

The basic principles of electrostatographic printing with dry marking material (hereinafter generally referred to as "xerography," "xerographic printing," and/or the like) are well known: a light image of an original to be copied is typically recorded in the form of a latent electrostatic image upon a photosensitive member with subsequent rendering of the latent image visible by the application of electroscopic marking particles, commonly referred to as toner. The visual toner image can be either fixed directly upon the photosensitive member or transferred from the member to another support, such as a sheet of plain paper, with subsequent affixing of the image thereto in one of various ways, for example, as by heat and pressure. To affix or fuse electroscopic toner material onto a support member by heat and pressure, the temperature of the toner material is typically elevated to a point at which its constituents coalesce and become tacky while and pressure is simultaneously applied, thus causing the toner to flow to some extent into the fibers or pores of the support member or otherwise upon the surface thereof. Thereafter, as the toner material cools, solidification of the toner material occurs and the toner material becomes bonded firmly to the support member.

One arrangement for minimizing some of the problems associated with heat and pressure fusing, particularly offsetting, has been to provide the fuser roll with an outer surface or covering of polytetrafluoroethylene, widely distributed under the trademark TEFLON®, to which a release agent such as silicone oil is applied, the thickness of the TEFLON®. material being on the order of several mils and the thickness of the oil being less than 1 micron. To ensure and maintain good release properties of the fuser roll, it has become customary to apply release agents to the fuser members to ensure that the toner is completely released from the fuser roll during the fusing operation. Typically, these materials are applied as thin films of, for example, silicone oils to prevent toner offset. Release agent management ("RAM") systems have been used as parts of roll fuser apparatuses for some time.

Xerographic printing devices are capable of printing with a normal color toner or with a special clear toner. Each toner requires a specific release agent or fuser fluid to be loaded. A technician has to know that they must manually load either a first type of fuser fluid like fuser shield, or second type such as a nominal fuser fluid in the RAM assembly of the device depending on what types of jobs will be printed that day, i.e., color or clear toner jobs. The technician must also manually modify system nonvolatile memory (NVM [A, B]) values to match the fuser fluid that has been loaded. A job that requires clear toner needs the first type (fuser shield) fuser fluid to be loaded in the RAM Assembly and the Fuser Ram Counter "A" NVM has to be manually set to an enabled value [1] and Fuser Ram Counter "B" NVM with a disabled value [0]. A job that requires regular colored toner needs the second type of (nominal) fuser fluid loaded in the RAM Assembly and the Fuser Ram Counter "B" NVM has to be manually set to an enabled value [1] and Fuser Ram Counter "A" NVM with a disabled value [0].

A mismatch of fuser fluid with toner like when nominal fuser oil is used for Clear printing, it leaves a messy clear toner residue throughout the paper path, which will translate into a long and expensive service call or the system may suffer from phantom jams due to sensors blocked with clear toner. There is no automatic error checking in the system today to ensure that the proper fuser oil is loaded to match the toner required by the job and the system will print with whatever oil is installed.

For the reasons stated above, and for other reasons stated below which will become apparent to those skilled in the art upon reading and understanding the present specification, there is a need in the art to prevent accidental oil and toner mismatches.

BRIEF SUMMARY OF THE INVENTION

Accordingly, an improved system and method is provided with which an automatic analysis of the fuser oil is performed to prevent accidental oil and toner mismatches by the insertion of a photovoltaic sensor and associated logic inline along the tube that delivers the fuser oil to the fuser.

DETAILED DESCRIPTION OF THE INVENTION

Figure 1:
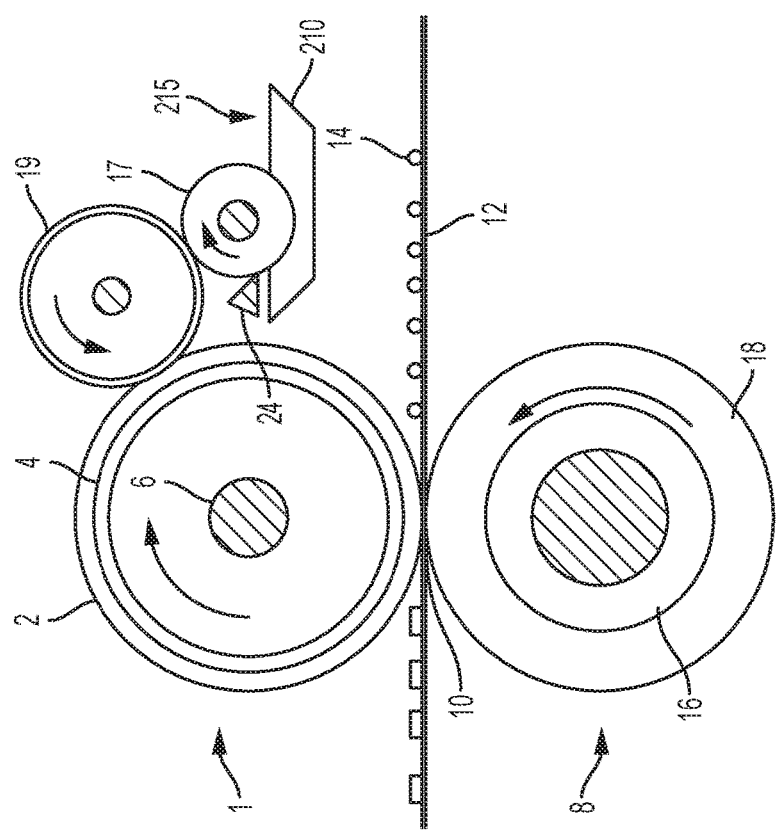
FIG. 1 is a schematic representation in cross-section of a fusing system of an electrostatographic printing machine which employs the thermally stabilized silicone liquid composition of the present invention.

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

With the introduction of clear toner to Xerographic printing, different fusing oil is required in order to ensure that the clear toner will reliably fix to the color toner on the page. The conventional oil will not work with the clear toner. When clear toner print jobs are run, the normal oil hardware is swapped out of the machine and a set of oiling hardware that uses this different fusing oil is inserted into the machine.

In addition, the operator must swap some memory locations of software to let the machine know the correct oil is installed. Using normal oil with clean toner (mismatch) leaves a messy clear toner residue throughout the paper path, which will translate into a long and expensive service call or the system may suffer from phantom jams due to sensors blocked with clear toner.

To prevent mismatches the disclosed embodiments propose the use of a Fuser Reservoir sensor to test the turbidity of the fuser oil. The addition of this turbidity sensor will allow the operator to know the state of the print engine fuser oil. The allowable limit would be predefined and could be media specific. The fuser oil turbidity sensor would be inside the fuser reservoir or at inlet before entering the reservoir. The fuser reservoir sensor will obtain the value in Nephelometric Turbidity Units (NTU) and the system will compare it to known NTU values and report it back to the operator.

Illustrative examples of the devices, systems, and methods disclosed herein are provided below. An embodiment of the devices, systems, and methods may include any one or more, and any combination of, the examples described below.

In one aspect, the disclosed embodiment relate to an apparatus useful in printing to monitor turbidity of release agent comprising an input element configured to select a first printing material from a plurality of printing materials; a moving member having an inner surface and an outer surface; a lubricant dispenser or oil dispenser to dispense a release agent on the moving member, wherein the lubricant dispenser comprises a reservoir containing the release agent and an inlet port for delivering the release agent to the reservoir; a turbidity sensor configured to measure turbidity of the release agent in the reservoir; a processor comprising a first detection module coupled to the input element and configured to generate a first detection signal according to the measured turbidity of the release agent when the measured turbidity indicates an error event; and a display device configured to display warning information when the first detection signal indicates an error event.

A further aspect of the disclosed embodiments relate to an apparatus wherein the turbidity sensor comprises a source configured to emit electromagnetic energy towards the reservoir and a receiver configured to receive at least some of the electromagnetic energy thereby generating electronic signals.

A further aspect of the disclosed embodiments relate to an apparatus wherein the turbidity sensor converts the electronic signals into Nephelometric Turbidity Units (NTU).

A further aspect of the disclosed embodiments relate to an apparatus wherein the processor converts the NTU values into high or low values.

A further aspect of the disclosed embodiments relate to an apparatus wherein selection of the first printing material is mapped as a high or a low value.

A further aspect of the disclosed embodiments relate to an apparatus wherein the first detection module being further configured to compare the selection of the first printing material to the measured turbidity of the release agent by using the mapped and converted high or low values.

A further aspect of the disclosed embodiments relate to an apparatus wherein the error event is generated when the mapped and converted high or low values do not match.

A further aspect of the disclosed embodiments relate to an apparatus wherein the first detection module is an XOR gate configured to generate the first detection signal according to the measured turbidity of the release agent.

A further aspect of the disclosed embodiments relate to an apparatus wherein the turbidity sensor is positioned inside the reservoir.

A further aspect of the disclosed embodiments relate to an apparatus wherein the turbidity sensor is positioned inline along the inlet port that carries the release agent to the reservoir.

In yet another aspect of the disclosed embodiments relate to a method for monitoring turbidity of release agent useful in printing comprising electing a first printing material from a plurality of printing materials; using a moving member having an inner surface and an outer surface; using a lubricant dispenser to dispense a release agent on the moving member, wherein the lubricant dispenser comprises a reservoir containing the release agent and an inlet port for delivering the release agent to the reservoir; using a turbidity sensor configured to measure turbidity of the release agent in the reservoir; processing using a processor comprising a first detection module coupled to the input element and configured to generate a first detection signal according to the measured turbidity of the release agent when the measured turbidity indicates an error event; and displaying warning information when the first detection signal indicates an error event.

Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. For example, "a plurality of resistors" may include two or more resistors.

The terms "print substrate" or "substrate" generally refers to a usually flexible, sometimes curled, physical sheet of paper, Mylar material, plastic, or other suitable physical substrate for images, whether precut or web fed.

As used herein, the term "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs). A processor is capable of executing computer-executable instructions or data structures stored thereon.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, and the like that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described therein.

As used herein, "turbidity" is the measurement of the amount of suspected solids in a solution (i.e., cloudiness or haziness of a liquid sample like fuser oil, release agent and the like) that causes light to be scattered or absorbed. Turbidity can be used to compare the clarity (or lack thereof) between gels, liquids, or the like. Turbidity may be measured in FTU (Formazin Turbidity Units), FNU (Formazin Nephelometric Units), or NTU (nephelometric turbidity units). An instrument called a nephelometer measures turbidity by measuring the amount of light scattered at an angle such as a 90-degree angle to the axis of the incident light.

Having thus outlined several embodiments of printing apparatus and processes, and described various sequences of operation, reference is now made to FIGS. 1-5 showing further embodiments. Unless otherwise noted, elements similar to those previously described will be given the same reference numerals and serve the same functions.

FIG. 1 is a schematic representation in cross-section of a fusing system of an electrostatographic printing machine which employs the thermally stabilized silicone liquid composition of the present invention. An electrostatographic printing machine is a device such as the Xerox iGen3® Digital Production Press, a printer or similar output device. The electrostatographic printing machine can be used to produce prints from various types of media, such as coated or uncoated (plain) paper sheets, at high speeds.

In the toner fusing area, the conventional silicone liquids used as release agents are commonly referred to as silicone oils. Thus, the silicone liquid may be referred herein as an oil. However, the term oil is not intended to limit the type of silicone liquid that can be thermally stabilized according to the present invention.

A typical fusing system of the present invention is described in conjunction with a fuser assembly as shown in FIG. 1 where the numeral 1 designates a fuser roll comprising elastomer surface 2 upon suitable base member 4 which is a hollow cylinder or core fabricated from any suitable metal such as aluminum, anodized aluminum, steel, nickel, copper, and the like, having a suitable heating element 6 disposed in the hollow portion thereof which is coextensive with the cylinder. Backup or pressure roll 8 cooperates with fuser roll 1 to form a nip or contact arc 10 through which a copy paper or other substrate 12 passes such that toner image 14 thereon contact elastomer surface 2 of fuser roll 1. As shown in FIG. 1, the backup roll 8 has a rigid steel core 16 with a soft surface layer 18 thereon. Sump 210 contains polymeric release agent 215 which may be a solid or liquid at room temperature, but is a fluid at operating temperatures.

In the embodiment shown in FIG. 1 for applying the polymeric release agent 215 to elastomer surface 2, two release agent delivery rolls 17 and 19 rotatably mounted in the direction indicated are provided to transport release agent from the sump 210 to the elastomer surface 2. As illustrated in FIG. 1, roll 17 is partly immersed in the sump 210 and transports on its surface release agent from the sump to the delivery roll 19. By using a metering blade 24 a layer of polymeric release fluid can be applied initially to delivery roll 19 and subsequently to the elastomer surface 2 in controlled thickness ranging from sub-micrometer thickness to a thickness of several micrometers of release fluid. Thus, by metering device 24 about 0.1 to 2 micrometers or greater thickness of release fluid can be applied to the elastomer surface 2.

As used herein, the phrase fuser system component may be a roll belt, flat surface or other suitable shape used in the fixing of thermoplastic toner images to a suitable substrate. It may take the form of a fuser member, a pressure member or a release agent donor member preferably in the form of a cylindrical roll. Typically, the fuser system component is made of a hollow cylindrical metal core, such as copper, aluminum, steel and like, and has an outer layer of the selected cured fluoroelastomer. Alternatively, there may be one or more intermediate layers between the substrate and the outer layer of the cured elastomer if desired. Typical materials having the appropriate thermal and mechanical properties for such layers include silicone elastomers, fluoroelastomers, silicone grafted fluoroelastomers, EPDM and Teflon PFA sleeved rollers. EPDM is ethylene propylene diene terpolymer and PFA is a Teflon copolymer containing tetrafluoroethylene monomer units along with perfluoroalkyl monomer units such as perfluorovinyl ether.

Figure 2:
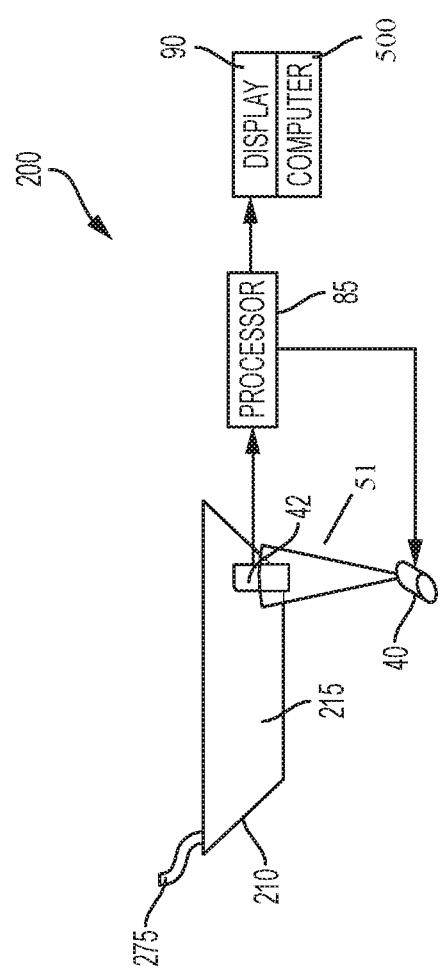
FIG. 2 schematically illustrates a particular example of various illustrative embodiments of an apparatus in accord with the present disclosure.

Having thus outlined several embodiments of printing apparatus and processes, and described various sequences of operation, reference is now made to FIG. 2 showing a further embodiment. Unless otherwise noted, elements similar to those previously described have been given the same reference numerals and serve the same functions. FIG. 2 is an illustration of an apparatus 200 for monitoring the turbidity of fuser oil in a fusing system such as described in FIG. 1.

Figure 3:
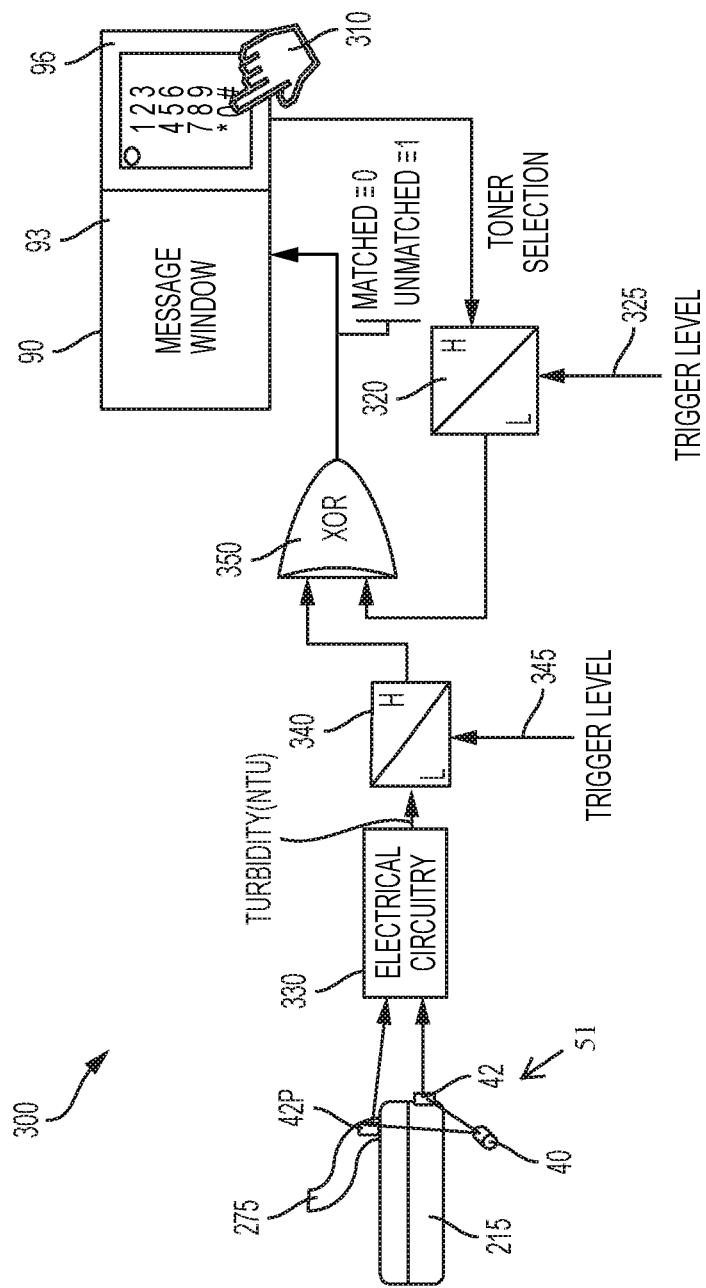
FIG. 3 is an illustrative representation of an exemplary arrangement of a source and receiver of a turbidity sensor used with an electronic device to prevent accidental oil and toner mismatches in accordance to an embodiment.

With reference to FIGS. 2 and 3, numeral 51 indicates as a whole an optical-type turbidity sensor for printing applications, typically a printer or xerographic device, of which only a tank/reservoir 210 is shown, provided with a reservoir seat (not shown) for the sensor 51 and in use full of a release agent or oil of the xerographic appliance, the physical features of which, such as optical absorbance (haziness/clarity) and possibly temperature, are intended to be measured.

In various illustrative embodiments, the release agent material 215 may include a functional silicone oil, for example. The apparatus 200 may also include a release agent metering roller like roller 17 supported for contact with the lubricant/oil dispenser of the release agent material 215. Lubricant/oil dispenser comprises a reservoir 210 containing release agent 215, and an inlet port 275 for delivering release agent 215 to the reservoir 210 and metering rollers (17&19) to the outer surface of fuser roller 1.

In conjunction with the lubricant dispenser there is shown a device for testing the turbidity of the fuser oil by using a turbidity sensor that comprises a source 40 and a receiver 42 coupled to a processor 85 which provides an indication of the turbidity of the oil, at or before it enters the reservoir 210, to a display device 90 and/or computer 500. An instrument called a nephelometer measures turbidity by measuring the amount of light scattered at an angle. Nephelometric measurements are based on the light-scattering properties of particles. The units of turbidity from a calibrated nephelometer are called Nephelometric Turbidity Units (NTU). The turbidity sensor 40.42,85 can detect, for example, a variation in the concentration of particles in the oil in the reservoir 210.

In one configuration, source 40 under the control of a regulator (not shown) or processor 86 is configured to emit electromagnetic energy such as a light towards reservoir 210. Receiver 42 is configured and positioned to receive at least some of the electromagnetic energy. It may be desirable to provide plural turbidity sensors in some configurations to monitor contamination of particulate material such as toner over time within the subject material at plural positions such as when the release agent 215 enters the reservoir via the input port 275 and changes over time. Utilizing one or more sensors, the rate of separation can be monitored providing information regarding the condition of the release material or slurry in reservoir 210. Unused release material and released material combined with toner is recycled back to the reservoir 210 which causes the material to become cloudy or hazy over multiple print runs.

Next, another embodiment of the present invention will be described. Note that portions which are the same as those in the previous embodiments described above are denoted by the same reference numerals, and descriptions of the same portions as those as in the prior embodiments will be omitted.

FIG. 3 is an illustrative representation of an exemplary arrangement of a source and receiver of a turbidity sensor used with an electronic device to prevent accidental oil and toner mismatches in accordance to an embodiment. The illustrated circuit 300 meets the need in the art for toner and fuser oil mismatch notification. The addition of this turbidity sensor will allow the operator to know the state of the print engine fuser oil in real-time.

Referring to FIG. 3, an alternative sensor configuration is illustrated as reference 300. The illustrated sensor configuration includes electrical circuitry coupled with receivers 42 and optional receiver 42P. In the case where an optional receiver is added such as receiver 42 a beam splitter (not shown) should be provided intermediate to source 40 to split the emitted signal and supply both receivers. Source 40 comprises a light emitting diode (LED) configured to emit infrared electromagnetic energy or to emit electromagnetic energy of another wavelength as dictated by the fluid being monitored. Receiver 42 may be implemented as a photodiode in an exemplary embodiment. Receiver 42 is configured to receive electromagnetic energy emitted from source 40 with a broad spectral range which detects at least 0-20 NTU. Electrical circuitry 330 receives the outputted signal from the receiver (42 or 42P) and conditions the signal converting the analog signals produced by the photodiodes into digital signals in NTU based upon an equation or a converting table. The source 40, receiver 42, and electronic circuitry produce a turbidity (NTU) value. Samples of the first type of fuser fluid like fuser shield have an NTU value of approximately 0.15. The second type like the nominal fuser fluid has an NTU value of 0.11. Note that the turbidity of the fuser shield is higher than the turbidity of the nominal fuser fluid by almost 40%.

FIG. 3 illustrates a circuit where two types of release agent oil can be compared to one or more toner types. This comparison can be scaled to include more than two release agents by adding additional circuits or by using the processing power of computer 500 with programming that includes tables and the like. For two fluids and for one or more toners a circuit having gates and comparator would be more than adequate to ascertain the matching. In the illustration, a selected toner dictates whether a fuser shield having 0.15 NTU of turbidity or a nominal fuser fluid having 0.11 NTU of turbidity is found in the reservoir.

A trigger level 345 can be set at comparator 340 to output a digital value [0, 1] based on the turbidity value from electrical circuit 330. Comparator 340 can be a Schmitt Trigger or the like which converts a signal to a digital output. The comparator retains its value until the input changes sufficiently to trigger a change. For example, comparator 340 can be set at 0.13 NTU and signals (values) that are 0.13 or higher can indicate a high turbidity (digital value of "1") release agent. Signals that are lower than 0.13 NTU would indicate a low turbidity release agent.

Using an input element configured to select a first printing material from a plurality of printing materials a user 310 can choose the toner to use for a printing job. The selection could be a code that identifies the tones such as for example clear toner or normal color toner. A lookup table (not shown) could then be used that maps the selection to the appropriate turbidity of the release agent or an indication that a high/low type of oil is better suited for the toner selection at 310. This selection can be the turbidity (NTU) of the release agent that is best suited for the toner being used. In the alternative, the selection could be an indication that a low turbidity (digital value "0") or a high turbidity fuser oil which is associated with the toner being used at the digital production press 110. The print media being used in combination with the toner selection to change the fuser oil turbidity that is needed to complete the print job. Based on the selection a comparator similar to 340 can be used with a same or different trigger level 325. Trigger level 325 can be supplemented to include allowable limit that would be predefined and could be media specific. Of course, in a high/low scenario comparator 320 is not needed and the digital value could be send to exclusive OR gate 350 for processing with the turbidity value as measured by the turbidity sensor. When the output of the exclusive OR gate 350 indicates a mismatch and is connected to enable the output terminal like display device 90 of printing apparatus 100. A message window 93 or an indicator capable of conveying to the user 310 warning information or conveying an error event that the combination of fuser oil and toner would compromise the printing quality. Using an indicator as a message conveyor can include illuminating a light-emitting diode (LED).

Figure 4:
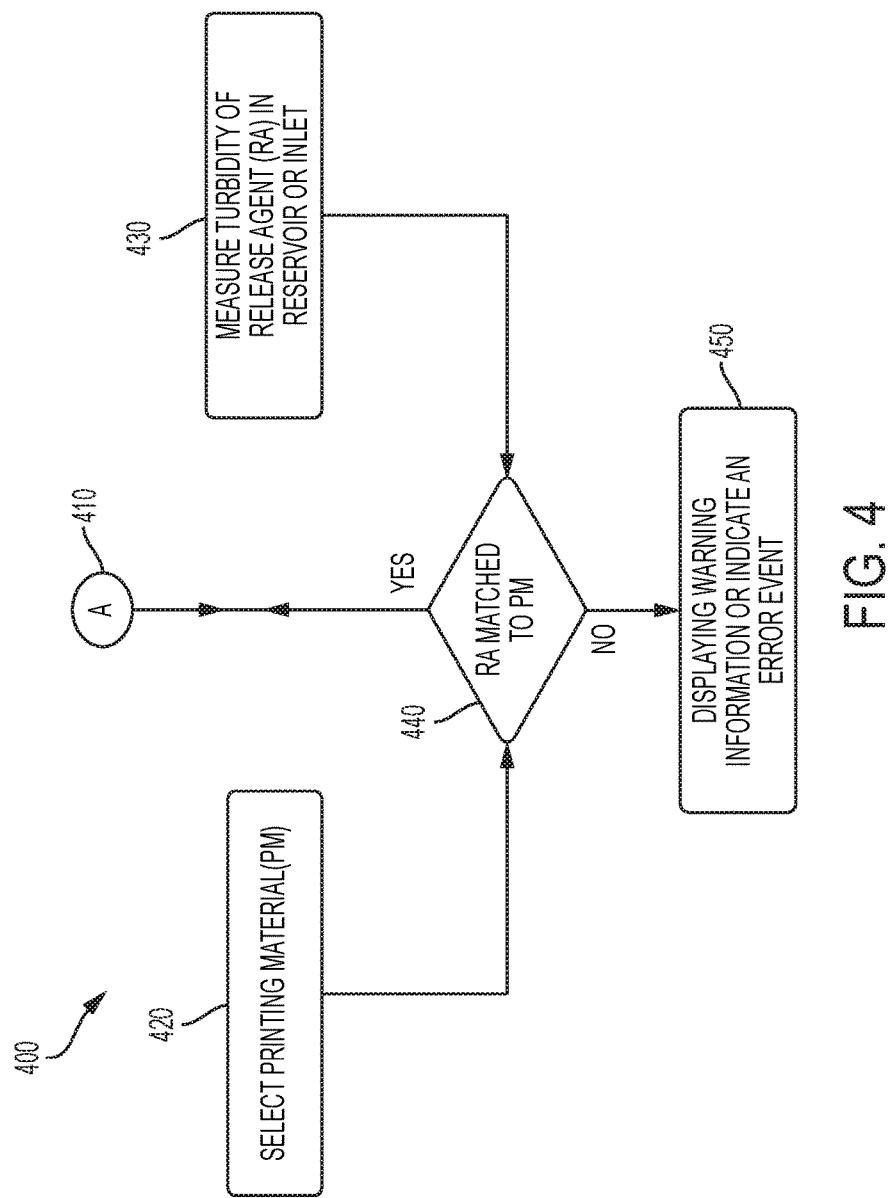
FIG. 4 is a flow chart of a method to prevent accidental oil and toner mismatches in a printing system in accordance to an embodiment; and, FIG. 5 illustrates a block diagram of an exemplary system for operating an image forming device with one or more particularly-configured external heat rolls according to this disclosure.

FIG. 4 is a flow chart of a method to prevent accidental oil and toner mismatches in a printing system in accordance to an embodiment.

In the previous section, a system level overview of the operation of an embodiment is described. In this section, the particular methods of such an embodiment are described by reference to a series of flowcharts. Describing the methods by reference to a flowchart enables one skilled in the art to develop such programs, firmware, or hardware, including such instructions to carry out the methods on suitable computers, executing the instructions from computer-readable media.

Figure 5:
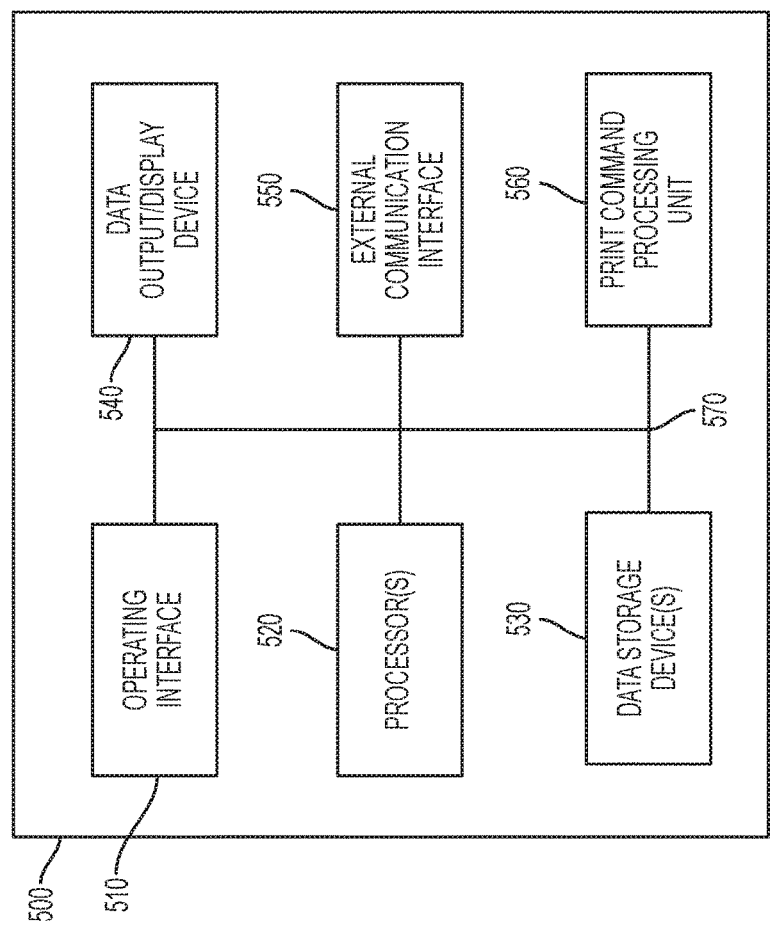

Methods 400 can be performed by a program executing on, or performed by firmware or hardware that is a part of, a computer, such as computer 500 in FIG. 5.

Method 400 begins at 410 when it is invoked at start up by printer 100, at the start of a print job, or as selected by a user through input device 96.

Action 440 determines if the release agent is matched to the toner being used for a print job by using the data provided by action 42, i.e., measured turbidity of release agent in reservoir 210 or inlet port 210 to the oil dispenser, and action 420, i.e., the selected printing material or clear/normal toner. When it is determined that there is a match between the toner and the release agent action 440 returns to program point "A" 410 which is the start of process 400. When action 440 determines that the toner and release agent are not matched then control is passed to action 450 where the process displays to the user warning information or indicates such by flashing an LED or writing a message that is indicative of an error event.

FIG. 5 illustrates a block diagram of an exemplary system 500 for operating an image forming device with one or more particularly-configured external heat rolls according to this disclosure.

Components of the exemplary system 500 shown in FIG. 5 may be, for example, housed in a user workstation, in a server or in an image forming device.

The exemplary system 500 may include an operating interface 510 by which a user may communicate with the exemplary system 500, or otherwise by which the exemplary system 500 may receive instructions input to it from another source. In instances where the operating interface 510 may be a locally accessible user interface, the operating interface 510 may be configured as one or more conventional mechanisms common to computing and/or image forming devices that permit a user to input information to the exemplary system 500. The operating interface 510 may include, for example, a conventional keyboard and mouse, a touchscreen with "soft" buttons or with various components for use with a compatible stylus, a microphone by which a user may provide oral commands to the exemplary system 500 to be "translated" by a voice recognition program, or other like device by which a user may communicate specific operating instructions to the exemplary system 500.

The exemplary system 500 may include one or more local processors 520 for individually operating the exemplary system 500 and for carrying out processing, assessment, reporting and control functions. Processor(s) 520 may include at least one conventional processor or microprocessor that interprets and executes instructions to direct specific operation and analysis functions with regard to image data that is commanded or intended to direct image forming in a specific image forming device with which the exemplary system 500 is associated.

The exemplary system 500 may include one or more data storage devices 530. Such data storage device(s) 530 may be used to store data or operating programs to be used by the exemplary system 500, and specifically the processor(s) 520, in carrying out the image forming control functions of the exemplary system 500. Data storage device(s) 530 may be used to collect information regarding any or all of the functions of the exemplary system 500. The data storage device(s) 530 may include a random access memory (RAM) or another type of dynamic storage device that is capable of storing collected information, and separately storing instructions for execution of system operations by, for example, processor(s) 520. Data storage device(s) 530 may also include a read-only memory (ROM), which may include a conventional ROM device or another type of static storage device that stores static information and instructions for processor(s) 520. Further, the data storage device(s) 530 may be integral to the exemplary system 500, or may be provided external to, and in wired or wireless communication with, the exemplary system 500.

The exemplary system 500 may include at least one data output/display device 540, which may be configured as one or more conventional mechanisms that output information to a user, including a display screen on a computing or image forming device, including a graphical user interface (GUI) on the image forming device. The data output/display device 540 may be usable to display to a user an indication of image forming data, and a selection of image receiving media, that may be evaluated to indicate a control function to mitigate adverse effects of excess toner contamination associated with a particular image forming operation in an image forming device. The data output/display device 340 may then be usable, in conjunction with the operating interface 310 to display to a user a series of options for optimized image forming operations in the image forming device.

The exemplary system 500 may include one or more separate external communication interfaces 550 by which the exemplary system 500 may communicate with components external to the exemplary system 500, or by which the exemplary system 500 may communicate with an image forming device with which the exemplary system 500 may be associated when it is not fully integral to the image forming device. No particular limiting configuration to the external communication interface(s) 550 is to be implied by the depiction in FIG. 5, other than that the external communication interface(s) 550 may be configured to connect to external components via one or more available wired or wireless communication links.

The exemplary system 500 may include a print command processing unit 560, which may be a part or a function of processor 520 coupled to, for example, one or more storage devices 530, or may be a separate stand-alone component module or circuit in the exemplary system 500. The print command processing unit 560 may review control and image data that specify an image forming operation to be carried out by the image forming device. The print command processing unit 560 may then control the image forming operation in the image forming device according to the control and image data, and particularly control heat levels in one or more heated roll components in the image forming device.

All of the various components of the exemplary system 500, as depicted in FIG. 5, may be connected by one or more data/control busses 570. These data/control busses 570 may provide wired or wireless communication between the various components of the exemplary system 500, whether all of those components are housed integrally in, or are otherwise external and connected to, the exemplary system 500.

It should be appreciated that, although depicted in FIG. 5 as what appears to be an integral unit, the various disclosed elements of the exemplary system 500 may be arranged in any combination of sub-systems as individual components or combinations of components, integral to a single unit, or external to, and in wired or wireless communication with the single unit of the exemplary system 500. In other words, no specific configuration as an integral unit or as a support unit is to be implied by the depiction in FIG. 5. Further, although depicted as individual units for ease of understanding of the details provided in this disclosure regarding the exemplary system 500, it should be understood that the described functions of any of the individually-depicted components may be undertaken, for example, by one or more processors 520 connected to, and in communication with, one or more data storage devices 530.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An apparatus useful in printing to monitor turbidity of release agent comprising:
    an input element configured to select a first printing material from a plurality of printing materials;
    a moving member having an inner surface and an outer surface;
    an oil dispenser to dispense a release agent on the moving member,
    wherein the oil dispenser comprises a reservoir containing the release agent and an inlet port for delivering the release agent to the reservoir;
    a turbidity sensor configured to measure turbidity of the release agent in the reservoir;
    a processor comprising a first detection module coupled to the input element and configured to generate a first detection signal according to the measured turbidity of the release agent when the measured turbidity indicates an error event; and a display device configured to display warning information when the first detection signal indicates an error event;

wherein the turbidity sensor comprises a source configured to emit electromagnetic energy towards the reservoir and a receiver configured to receive at least some of the electromagnetic energy thereby generating electronic signals;

wherein the turbidity sensor converts the electronic signals into Nephelometric Turbidity Units (NTU);

wherein the processor converts the NTU values into high or low values;

wherein selection of the first printing material is mapped as a high or a low value;

wherein the first detection module being further configured to compare the selection of the first printing material to the measured turbidity of the release agent by using the mapped and converted high or low values.

2. A method for monitoring turbidity of release agent useful in printing comprising:

selecting a first printing material from a plurality of printing materials;

using a moving member having an inner surface and an outer surface;

using an oil dispenser to dispense a release agent on the moving member, wherein the oil dispenser comprises a reservoir containing the release agent and an inlet port for delivering the release agent to the reservoir;

using a turbidity sensor configured to measure turbidity of the release agent in the reservoir;

processing using a processor comprising a first detection module coupled to the input element and configured to generate a first detection signal according to the measured turbidity of the release agent when the measured turbidity indicates an error event; and displaying warning information when the first detection signal indicates an error event;

wherein the turbidity sensor comprises a source configured to emit electromagnetic energy towards the reservoir and a receiver configured to receive at least some of the electromagnetic energy thereby generating electronic signals;

wherein the first detection module comparing the selection of the first printing material to the measured turbidity of the release agent by using mapped and converted values.

3. The apparatus according to claim 1, wherein the error event is generated when the mapped and converted high or low values do not match.

4. The apparatus according to claim 1, wherein the first detection module is an XOR gate configured to generate the first detection signal according to the measured turbidity of the release agent.

5. The apparatus according to claim 1, wherein the turbidity sensor is positioned inside the reservoir.

6. The apparatus according to claim 1, wherein the turbidity sensor is positioned inline along the inlet port that carries the release agent to the reservoir.

7. The method according to claim 2, wherein the turbidity sensor converts the electronic signals into Nephelometric Turbidity Units (NTU).

8. The method according to claim 7, wherein the processor converts the NTU values into high or low values.

9. The method according to claim 8, wherein selection of the first printing material is mapped as a high or a low value.

10. The method according to claim 9, wherein the error event is generated when the mapped and converted high or low values do not match.

11. The method according to claim 9, wherein the first detection module is an XOR gate configured to generate the first detection signal according to the measured turbidity of the release agent.

12. The method according to claim 7, wherein the turbidity sensor is positioned inside the reservoir.

13. The method according to claim 7, wherein the turbidity sensor is positioned inline along the inlet port that carries the release agent to the reservoir.

* * * * *